US006313289B1

(12) United States Patent
Ludescher et al.

(10) Patent No.: US 6,313,289 B1
(45) Date of Patent: Nov. 6, 2001

(54) PURIFICATION PROCESS

(75) Inventors: Johannes Ludescher, Breitenbach; Ludwig Miller; Hubert Sturm, both of Innsbruck; Werner Veit, Kufstein; Martin Decristoforo, Wattens; Siegfried Wolf, Brixlegg, all of (AT)

(73) Assignee: Biochemie Gesellschaft m.b.H., Kundl (AT)

( * ) Notice: Subject to any disclaimer, the term of this patent is extended or adjusted under 35 U.S.C. 154(b) by 0 days.

(21) Appl. No.: 09/341,542

(22) PCT Filed: Jan. 14, 1998

(86) PCT No.: PCT/EP98/00190

§ 371 Date: Aug. 4, 1999

§ 102(e) Date: Aug. 4, 1999

(87) PCT Pub. No.: WO98/31868

PCT Pub. Date: Jul. 23, 1998

(30) Foreign Application Priority Data

Jan. 16, 1997  (AT) ........................................ A 62/97

(51) Int. Cl.[7] ..................... C07D 501/04; C07D 501/22; C07D 417/12

(52) U.S. Cl. ........................................... 540/222; 548/170

(58) Field of Search ............................. 540/222; 548/170

(56) References Cited

U.S. PATENT DOCUMENTS 4,409,214 * 10/1983 Takaya .................. 540/222
5,574,154 * 11/1996 Abu-Nasrieh ................ 540/222

FOREIGN PATENT DOCUMENTS

| 030630 | * 6/1981 | (EP) . |
| 0 030 630 A | 6/1981 | (EP) . |
| 98/06723 | * 2/1998 | (WO) . |
| 99/51607 | * 10/1999 | (WO) . |

* cited by examiner

Primary Examiner—Mark L. Berch
(74) Attorney, Agent, or Firm—Lydia T. McNally

(57) ABSTRACT

Crystalline 2-(amninothiazol-4-yl)-2-(tert.butoxycarbonylmethoxyimino)acetic acid-S-mercapto-benzo-thiazolylester in form of an N,N-dimethylacetamide solvate; a crystalline salt of a 7-[2-(aminothiazol-4-yl)-2-(carboxymethoxyimino)acetamido]-3-vinyl-3-cephem-4-carboxylic acid with an amine of formula $N(R_1)(R_2)(R_3)$, wherein $R_1$, $R_2$, and $R_3$ have various meanings, a crystalline sulphuric acid addition salt of a 7-[2-(2-aminothiazol-4-yl)-2-carboxymethoxyimino)acetamido]-3-vinyl-3-cephem-4-carboxylic acid; and the use of these salts in the production of cefixime, e.g. in form of a trihydrate.

12 Claims, No Drawings

PURIFICATION PROCESS

The present invention relates to a process for the purification of cefixime.

Cefixime of formula

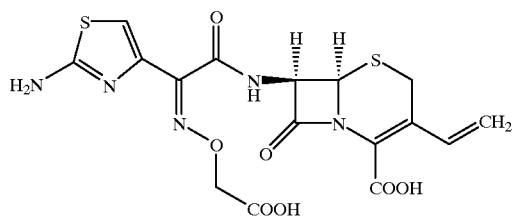

e.g. in form of a trihydrate, is a modern, orally available cephalosporin antibiotic having excellent antibacterial properties and high β-lactamase stability (see for example H. Yamanaka et al., J. Antibiotics (1985), 38(12), pp. 1738–1751).

According to prior art cefixime may e.g. be produced by reacting a 7-amino-3-vinyl-3-cephem-4-carboxylic acid, e.g. of formula

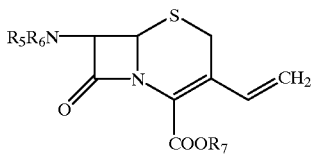

wherein $R_5$ and $R_6$ denote hydrogen or a leaving group and $R_7$ denotes hydrogen, alkyl, cycloalkyl, alkylaryl, aryl or arylalkyl; such as 7-amino-3-vinyl-3-cephem-4-carboxylic acid of formula

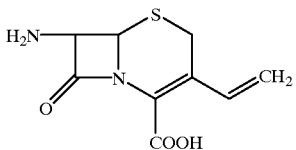

with a 2-(aminothiazol-4-yl)-2-(carboxymethoxyimino) acetic acid of formula

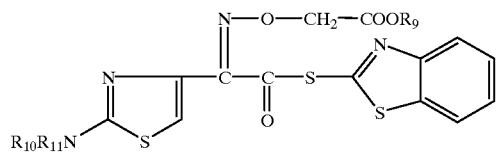

wherein $R_9$ denotes alkyl, cycloalkyl, alkylaryl, aryl or arylalkyl and $R_{10}$ and $R_{11}$ denote hydrogen, silyl or acyl, e.g. in a reactive form, such as 2-(aminothiazol-4-yl)-2-(tert.butoxycarbonylmethoxyimino)acetic acid-S-mercaptobenzo-thiazolylester of formula

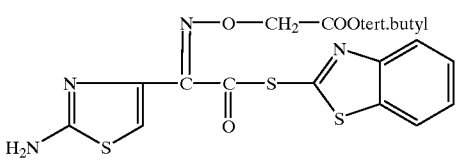

to give a 7-[2-(aminothiazol-4-yl)-2-(carboxymethoxyimino)acetamido]-3-vinyl-3-cephem-4-carboxylic acid, e.g. of formula

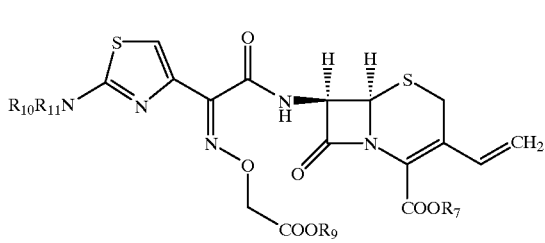

wherein $R_7$, $R_9$, $R_{10}$ and $R_{11}$ are as defined above, e.g. 7-[2-(aminothiazol-4-yl)-2-(tert.butoxycarbonylmethoxyimino)acetamido]-3-vinyl-3-cephem-4-carboxylic acid of formula

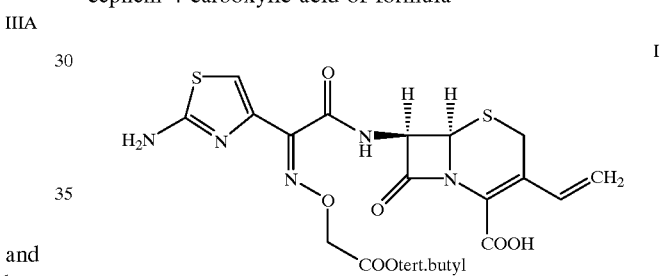

and splitting off a group $R_9$, such as tert.butyl, and, if present, any $R_7$ and/or $R_{11}$ which is not hydrogen, to obtain cefixime of formula II, e.g. in form of a trihydrate.

Prior Art Processes May Have Disadvantages.

A compound of formula IA, e.g. of formula I, may be obtained in amorphous form. It was found that, due to its high solubility, solvents such as ethers having in general a low solubilizing effect are to be used for its isolation, e.g. according to EP 030 630 (see e.g. example 53) and thus undesired by-products which have to be separated off may be precipitated beside a compound of formula IA, e.g. of formula I. Isolation of a compound of formula IA, e.g. of formula I in free acid form may also be effected from water but removal of water causes difficulties in a subsequent drying process.

Removal of protecting groups of a compound of formula IA, e.g. of formula I under acidic conditions to obtain cefixime may cause difficulties, e.g. purification is to be carried out via chromatography as e.g. described in H. Yamanaka et al., J. Antibiotics (1985), 38(12), pp. 1738–1751) (yield of 34.1%) and in AU 9526702 (WO 95/33753). According to EP 030 630, example 168, cefixime is precipitated after splitting off protecting groups by addition of diisopropylether having in general a low solubilizing effect and thus undesired by-products may additionally be precipitated.

According to the present invention surprisingly a new process for the production of cefixime in highly pure form has been found. The process according to the present invention may avoid disadvantages of prior art, e.g. by provision of intermediates, such as compounds of formulae I, II and optionally IV in crystalline form, which may have a high purification effect on the end product cefixime.

In one aspect the present invention provides a process for the production of cefixime of formula II, comprising a. reacting a 7-amino-3-vinyl-3-cephem-4-carboxylic acid of formula IIIA, wherein $R_5$ and $R_6$ denote hydrogen or a leaving group and $R_7$ denotes hydrogen, alkyl, cycloalkyl, alkylaryl, aryl, arylalkyl or silyl, e.g. 7-amino-3-vinyl-3-cephem-4-carboxylic acid of formula III; e.g. in free form or in form of a salt, with a 2-(aminothiazol-4-yl)-2-carboxymethoxyimino)acetic acid of formula IVA, wherein $R_9$ denotes alkyl, cycloalkyl, alkylaryl, aryl or arylalkyl, $R_{10}$ denotes hydrogen and $R_{11}$ denotes hydrogen, silyl or acyl, e.g. 2-(aminothiazol-4-yl)-2-(tert.butoxycarbonyl-methoxyimino)acetic acid-S-mercaptobenzo-thiazolylester of formula IV; e.g. in free form or in form of a salt and/or in form of a solvate, e.g. an N,N-dimethylacetamide solvate;

to give a 7-[2-(aminothiazol-4-yl)-2-(carboxymethoxyimino)-acetamido]-3-vinyl-3-cephem-4-carboxylic acid of formula IA wherein $R_7$, $R_9$, $R_{10}$ and $R_{11}$ are as defined above, e.g. in free form or in form of a salt, e.g. 7-[2-(aminothiazol-4-yl)-2-(carboxymethoxyimino)acetamido]-3-vinyl-3-cephem-4-carboxylic acid of formula I;

b. reacting a 7-[2-(aminothiazol-4-yl)-2-(carboxymethoxyimino)-acetamido]-3-vinyl-3-cephem-4-carboxylic acid of formula IA, wherein $R_7$, $R_9$, $R_{10}$ and $R_{11}$ are as defined above, e.g. 7-[2-(aminothiazol-4-yl)-2-(carboxymethoxyimino)-acetamido]-3-vinyl-3-cephem-4-carboxylic acid of formula I, with an amine of formula

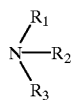

VI wherein $R_1$, $R_2$ and $R_3$ independently of each other denote hydrogen, alkyl, cycloalkyl, alkylaryl, aryl or aralkyl, to give a crystalline salt of a compound of formula IA, wherein $R_7$, $R_9$, $R_{10}$ and $R_{11}$ are as defined above, e.g. of formula I, with an amine of formula VI, wherein $R_1$, $R_2$ and $R_3$ are as defined above, c. reacting the crystalline salt of a compound of formula IA, wherein $R_7$, $R_9$, $R_{10}$ and $R_{11}$ are as defined above with an amine of formula VI, wherein $R_1$, $R_2$ and $R_3$ are as defined above, with sulphuric acid to obtain a 7-[2-(aminothiazol-4-yl)-2-(carboxymethoxyimino)-acetamido]-3-vinyl-3-cephem-4-carboxylic acid, e.g. of formula

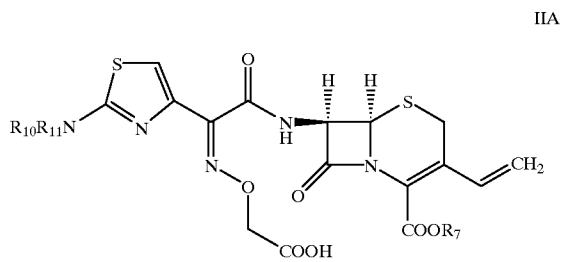

IIA wherein $R_7$, $R_{10}$ and $R_{11}$ are as defined above, e.g. a 7-[2-(aminothiazol-4-yl)-2-(carboxymethoxyimino)-acetamido]-3-vinyl-3-cephem-4-carboxylic acid of formula II, in form of a crystalline sulphuric acid addition salt, and, if desired, d. converting a sulphuric acid addition salt of a compound of formula IIA, wherein $R_9$, $R_{10}$ and $R_{11}$ are as defined above, e.g. a sulphuric acid addition salt of a compound of formula II, into cefixime of formula II, e.g. in form of a solvate, such as a hydrate, e.g. trihydrate.

Any starting compound described herein may be produced as described herein, or according to, e.g. analogous, known methods.

Step A. May Be Carried Out As Follows:

A 7-amino-3-vinyl-3-cephem-4-carboxylic acid, e.g. of formula IIIA, wherein $R_5$ and $R_6$ denote hydrogen or a leaving group, including e.g. a silyl group, e.g. $R_7$ denotes hydrogen and $R_6$ denotes hydrogen or a silyl group, preferably hydrogen; and $R_7$ denotes a group as e.g. described for a corresponding group in e.g. H. Yamanaka et al., J. Antibiotics (1985), 38(12), pp.1738–1751, AU 9526702 (WO 95/33753) and EP 030 630, the content of which is introduced herein by reference, and e.g. including hydrogen, alkyl, such as lower alkyl, e.g. tert.butyl, cycloalkyl, alkylaryl, e.g. (lower alkyl)aryl, arylalkyl, e.g. benzhydryl, or silyl; such as hydrogen, alkyl or arylalkyl, preferably hydrogen; in free form or in form of a salt, e.g. an acid addition salt or, in case that $R_7$ denotes hydrogen, in form of a salt of the carboxylic acid group with a base, e.g. an amine salt; preferably in form of an amine salt; including e.g. a compound of formula III; may be reacted with a 2-(aminothiazol-4-yl)-2-(carboxymethoxyimino)acetic acid, e.g. of formula IVA, wherein $R_9$, $R_{10}$ and $R_{11}$ denote a group as e.g. described for a corresponding group in e.g. H. Yamanaka et al., J. Antibiotics (1985), 38(12), pp.1738–1751, AU 9526702 (WO 95l33753) and EP 030 630; the content of which is introduced herein by reference; and including in the meaning of $R_9$ alkyl, cycloalkyl, alkylaryl, aryl or arylalkyl, preferably alkyl, such as lower alkyl, e.g. butyl such as tert.butyl; and in the meaning of $R_{10}$ and $R_{11}$ hydrogen, silyl or acyl, e.g. $R_{10}$ denotes hydrogen and $R_{11}$ denotes hydrogen, silyl or acyl, e.g. formyl, alkanoyl, such as acetyl, or aralkanoyl, such as benzoyl, preferably formyl or hydrogen, e.g. hydrogen;

e.g. in form of an active derivative of a 2-(arninothiazol-4-yl)-2-(carboxymethoxyimino)-acetic acid such as e.g. described in H. Yamanaka et al., J. Antibiotics (1985), 38(12), pp. 1738–1751, AU 9526702 (WO 95/33753), EP 030 630 and U.S. Pat. No. 5,003,073, the content of which is introduced herein by reference; in free form, and in salt form and/or solvate form; preferably with 2-(aminothiazol-4-yl)-2-(tert.butoxycarbonylmethoxyimino)acetic acid-S- mercaptobenzo-thiazolylester of formula IV, e.g. in solvate form, such as in form of an N,N-dimethylacetamide solvate.

It was found that an N,N-dimethylacetamide solvate of a compound of formula IV is particularly useful in a process of the present invention because it may be obtained in highly pure, e.g. crystalline form and it may be used as such, e.g. in a reaction, e.g. acylation, of a 3-vinyl-3-cephem-4-carboxylic acid. An N,N-dimethylacetamide solvate of a compound of formula IV may be obtained by dissolving 2-(aminothiazol-4-yl)-2-(tert.butoxycarbonyl-methoxyimino)acetic acid S-mercapto-benzthiazolyl ester in N,N-dimethylacetamide at appropriate temperature, e.g. around room temperature, such as at room temperature. An anti-solvent, such as a nitrile, e.g. acetonitrile, an ester, such as ethyl acetate, an ether, such as methyl-tert.butylether or water may be present in the reaction mixture. A compound of formula IV in form of an N,N-dimethylacetamide solvate may crystallize. The amount of N,N-dimethylsolvate is not critical. Conveniently per gram of a compound of formula I e.g. 0.5 ml to 4 ml, preferably 1 ml to 3 ml, such as 1.5 ml to 2.5 ml N,N-dimethylacetamide may be used. 2-(Aminothiazol-4-yl)-2-(tert.butoxycarbonylmethoxyimino)acetic acid-S-mercapto-benzthiazolylester may also be isolated directly from a reaction mixture for its production, obtainable e.g. from a reaction of 2-(aminothiazol-4-yl)-2-tert.butoxycarbonylmethoxyimino)acetic acid with benzthiazolyl disulfid and triphenylphosphine, in form of an, e.g. crystalline, N,N-dimethylacetamide solvate.

A crystalline compound of formula IV obtained may be isolated, e.g. filtrated off. A compound of formula IV in form of an N,N-dimethylacetamide solvate is new and forms also part of the present invention.

In another aspect the present invention provides a process as described above wherein a 2-(aminothiazol-4-yl)-2-(carboxymethoxyimino)acetic acid is 2-(aminothiazol-4-yl)-2-(tert.butoxycarbonylmethoxyimino)acetic acid S-mercaptobenzo-thiazolylester, e.g. of formula IV, e.g. in form of an N,N-diacetamide solvate;

and 2-(aminothiazol-4-yl)-2-(tert.butoxycarbonylmethoxyimino)acetic acid S-mercaptobenzo-thiazolylester, e.g. of formula IV, in form of an N,N-dimethylacetamide solvate.

A reaction of a 7-amino-3-vinyl-3-cephem-4-carboxylic acid with a 2-(aminothiazol-4-yl)-2-(carboxymethoxyimino)acetic acid may be carried out as conventional, e.g. according to a, e.g. analogous, method, as e.g. described in H. Yamanaka et al., J. Antibiotics (1985), 38(12), pp. 1738–1751, AU 9526702 (WO 95/33753), EP 030 630 and U.S. Pat. No. 5,003,073.

In a preferred embodiment of the present invention a 7-amino-3-vinyl-3-cephem-4-carboxylic acid, e.g. of formula III, e.g. in form of a salt, such as an amine salt, including e.g. a salt with a tertiary amine, such as triethylamine or tributylamine, an amidine such as 1,5-diazabicyclo[4.3.0]non-5-ene (DBN) or 1,8-diazabicyclo [5.4.0]undec-7-ene (DBU) or a guanidine such as tetramethyl guanidine, preferably triethylamine;

may be reacted in an organic solvent, including for example a halogenated hydrocarbon such as dichloromethane, an ester such as ethyl acetate or butyl acetate and a ketone, such as methyl isobutyl ketone, preferably an ester, such as ethyl acetate; and, if desired, in the presence of a co-solvent, such as an alcohol, for example ethanol or methanol, water or an amide such as dimethylformamide, preferably water; or mixtures of individual solvents, e.g. as described above;

with a 2-(aminothiazol-4-yl)-2-(carboxymethoxyimino) acetic acid, for example in form of a reactive derivative, such as a 2-(aminothiazol-4-yl)-2-(tert.butoxycarbonylmethoxy-imino)acetic acid-S-mercapto-benzothiazolyl ester, e.g. of formula IV, e.g. in form of an N,N-dimethylacetamide solvate;

at appropriate temperatures, e.g. below, about at, or above room temperature; such as from about 0° C. to about 60° C., e.g. from 0° C. to 60° C.; such as from 10° C. to 50° C., e.g. at room temperature.

A 7-[2-(aminothiazol-4-yl)-2-(carboxymethoxyimino) acetamido]-3-vinyl-3-cephem-4-carboxylic acid of formula IA, e.g. a compound of formula I, e.g. in form of a salt with an amine, e.g. a tertiary amine may be obtained.

For the isolation of a 7-[2-(aminothiazol-4-yl)-2-(carboxymethoxyimino)acetamido]-3-vinyl-3-cephem-4-carboxylic acid, e.g. of formula IA, such as of formula I, water may be added to the reaction mixture, e.g. in the presence of a base, such as an amine, a bicarbonate or hydroxide, e.g. potassium, sodium. The phases formed may be separated. The aqueous phase may contain a compound of formula I, e.g. in form of a salt, e.g. with an amine, e.g. a tertiary amine. The aqueous mixture may be acidified, e.g. to obtain an pH of 1.5 to 3, e.g. 2 to 2.5, e.g. by addition of an acid, e.g. an inorganic acid, for example phosphoric acid; an organic solvent, e.g. a solvent as described above, preferably ethyl acetate, may be added, if desired and the aqueous and the organic phase may be separated. The organic phase may contain a 7-[2-(aminothiazol-4-yl)-2-(carboxymethoxyimino)acetamido]-3-vinyl-3-cephem-4-carboxylic acid, e.g. of formula IA, e.g. a compound of formula I, in free form. Any $R_7$ and/or $R_{11}$ which is other than hydrogen, e.g. as described above, may be split off as appropriate, e.g. as conventional, to obtain a 7-[2-(aminothiazol-4-yl)-2-(carboxymethoxyimino)acetamido]-3-vinyl-3-cephem-4-carboxylic acid wherein the amine group in the thiazolyl ring and/or the carboxylic group in position 4 may be free, e.g. a compound of formula I.

Step B. May Be Carried Out As Follows:

A 7-[2-(aminothiazol-4-yl)-2-(carboxymethoxyimino) acetamido]-3-vinyl-3-cephem-4-carboxylic acid, e.g. of formula IA, wherein $R_7$, $R_9$, $R_{10}$ and $R_{11}$ are as defined above, in free form or in salt form, e.g. 7-[2-(aminothiazol-4-yl)-2-(butoxycarbonylmethoxyimino)-acetamido]-3-vinyl-3-cephem-4-carboxylic acid of formula I, may be reacted with an an amine of formula VI, wherein $R_1$, $R_2$ and $R_3$ are as defined above, e.g. $R_1$, $R_2$ and $R_3$ independently of each other denote hydrogen, alkyl, cycloalkyl, aralkyl, aryl or alkylaryl, e.g. hydrogen, alkyl, cycloalkyl or aralkyl, such as hydrogen, alkyl or cycloalkyl. Preferably $R_1$, $R_2$ and $R_3$ each denotes cycloalkyl or alkyl, preferably alkyl, e.g. lower alkyl; such as ethyl; or $R_1$ and $R_2$ denote alkyl or cycloalkyl, preferably cycloalkyl and $R_3$ denote hydrogen; or $R_1$ and $R_2$ denote hydrogen and $R_3$ denotes alkyl or cycloalkyl, preferably alkyl, such as ($C_{1-12}$)alkyl; using e.g. per equivalent of a 7-[2-(aminothiazol-4-yl)-2-(carboxymethoxyimino)acetamido]-3-vinyl-3-cephem-4-carboxylic acid about e.g. 1 to 3, preferably 1 to 2 equivalents of an amine of formula VI;

e.g. in the presence of an organic solvent including for example an ester, e.g. an acetic acid ester, such as ethyl acetate or butyl acetate, a ketone, for example a dialkylketone, such as methyl isobutyl ketone and a chlorinated hydrocarbon, such as a chlorinated alkane, for example dichloromethane; if desired in the presence of a co-solvent, such as an alcohol, for example methanol, ethanol and isopropanol or water. An appropriate reaction temperature includes a temperature below, about at, or above room temperature; such as from about 0° C. up to the boiling point of a solvent used, e.g. under the reaction conditions, preferably, e.g. in case that dichloromethane is used as a solvent, about 0° to the boiling point of the solvent (mixture), including dichloromethane, used in the reaction mixture, such as about 10° C. to 50° C.

If not otherwise defined herein alkyl includes $(C_{1-22})$ alkyl, e.g. $(C_{1-18})$alkyl, such as $(C_{1-12})$alkyl, e.g. $(C_{1-10})$ alkyl, e.g. $(C_{1-6})$alkyl, such as $(C_{1-6})$alkyl, e.g. $(C_{1-4})$alkyl. Lower alkyl includes $(C_{1-6})$alkyl, e.g. $(C_{1-5})$alkyl, for example $(C_{1-4})$alkyl. Cycloalkyl includes $(C_{3-8})$cycloalkyl, such as $(C_{4-7})$cycloalkyl, e.g. $(C_{5-6})$cycloalkyl. Aryl includes $(C_{5-18})$aryl, such as $C_{(6-12)}$ aryl, preferably phenyl, napthyl, e.g. phenyl. Silyl includes a silyl protecting group, e.g. a conventional silyl protecting group, such as trialkylsilyl, for example trimethylsilyl. A leaving group includes groups which may easily be split off, e.g. during an acylation reaction; including e.g. a silyl group. An acyl group includes $(C_{1-24})$acyl, such as formyl, alkanoyl, aralkanoyl, aroyl and alkylaroyl, preferably formyl.

A crystalline salt of a 7-[2-(aminothiazol-4-yl)-2-(carboxymethoxyimino)acetamido]-3-vinyl-3-cephem-4-carboxylic acid, e.g. of formula IA, wherein $R_7$, $R_9$, $R_{10}$ and $R_{11}$ are as defined above, e.g. 7-[2-(aminothiazol-4-yl)-2-(butoxycarbonylmethoxyimino)acetamido]-3-vinyl-3-cephem-4-carboxylic acid of formula I, with an amine of formula VI, wherein $R_1$, $R_2$ and $R_3$ are as defined above, may be isolated from the reaction mixture, e.g. as appropriate, e.g. by filtration. Start and completion of crystallisation may be improved, e.g. by dilution of the reaction mixture, e.g. with a solvent as described above, such as a solvent which was used for the reaction to obtain that amine salt; and/or, in case that a co-solvent, e.g. an alcohol was used, e.g. in reaction step b. by distilling off that co-solvent, if appropriate.

A crystalline salt of a 7-[2-(aminothiazol-4-yl)-2-(carboxymethoxyimino)acetamido]-3-vinyl-3-cephem-4-carboxylic acid, e.g. a compound of formula IA, wherein $R_7$, $R_9$, $R_{10}$ and $R_{11}$ are as defined above, such as of formula I, with an amine of formula VI, wherein $R_1$, $R_2$ and $R_3$ are as defined above, may improve the purity of the end product, e.g. cefixime, because it was found that it may be obtained in high purity. A crystalline salt of a compound of formula IA with an amine of formula VI is new and also forms part of the present invention.

In another aspect the present invention provides a salt of a compound of formula IA, wherein $R_7$, $R_9$, $R_{10}$ and $R_{11}$ are as defined above, such as of formula I, with an amine of formula VI, wherein $R_1$, $R_2$ and $R_3$ are as defined above, e.g. triethylamine, dicyclohexylamine or tert.octylamine; in crystalline form.

A crystalline salt of a 7-[2-(aminothiazol-4-yl)-2-(tert.butoxy-carbonylmethoxyimino)acetamido]-3-vinyl-3-cephem-4-carboxylic acid, e.g. of a compound of formula IA, such as of formula I, with an amine of formula VI may also be obtained directly from a reaction mixture obtained in a reaction step a., e.g. in the presence of an amine of formula VI, without the isolation of a 7-[2-(aminothiazol-4-yl)-2-(carboxymethoxyimino)acetamido]-3-vinyl-3-cephem-4-carboxylic acid produced e.g. in a reaction step a.

A crystalline salt of a 7-[2-(aminothiazol-4-yl)-2-(carboxymethoxyimino)acetamido]-3-vinyl-3-cephem-4-carboxylic acid, e.g. of formula IA, wherein $R_7$, $R_9$, $R_{10}$ and $R_{11}$ are as defined above, such as of formula I, with an amine of formula VI may be converted into a highly pure 7-[2-(aminothiazol-4-yl)-2-(carboxymethoxyimino)acetamido]-3-vinyl-3-cephem-4-carboxylic acid wherein $R_7$, $R_9$, $R_{10}$ and $R_{11}$ are as defined above, such as of formula I, in free form; e.g. in the presence of an acidic agent, e.g. an inorganic or organic acid. Any $R_7$ and/or $R_{11}$ which is other than hydrogen, e.g. as described above, may be removed, e.g. as usual, to obtain a 7-[2-(aminothiazol-4-yl)-2-(carboxymethoxyimino)-acetamido]-3-vinyl-3-cephem-4-carboxylic acid wherein the amine group in the thiazolyl ring and/or the carboxylic group in position 4 of the ring system may be free, e.g. to obtain a compound of formula I.

Step C. May Be Carried Out As Follows:

A 7-[2-(aminothiazol-4-yl)-2-(carboxymethoxyimino) acetamido]-3-vinyl-3-cephem-4-carboxylic acid, e.g. of formula IA, wherein $R_7$, $R_9$, $R_{10}$ and $R_{11}$ are as defined above, such as of formula I, e.g. in free form or in salt form, such as in amine salt form, e.g. in form of a salt with an amine of formula VI, e.g. as obtainable in reaction step b., may be converted into a compound of formula

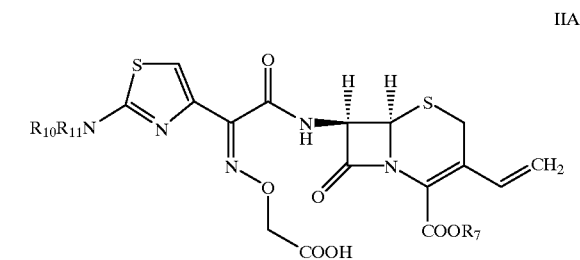

IIA wherein $R_7$, $R_{10}$ and $R_{11}$ are as defined above, e.g. a compound of formula II, in free form, salt form and/or solvate, e.g. hydrate, such as monohydrate form, e.g. in crystalline form, by treatment with sulphuric acid;

e.g. in an organic, e.g. polar, solvent or solvent mixture, including e.g. a nitrile, such as acetonitrile; if desired in the presence of a co-solvent including water, a sulphoxide, e.g. dimethyl sulphoxide or sulpholane, or mixtures of individual solvents, e.g. as described above; e.g. in the presence of an acid, e.g. organic, such as formic acid, acetic acid. The amount of sulphuric acid which may be used is not critical. In principle per equivalent of a compound of formula IA, e.g. of formula I, about 1 to 3, e.g. 1 to 2 equivalents may be used. If a compound of formula IA, e.g. of formula I, is used in form of a salt with a base, such as an amine, e.g. an amine of formula VI, the amount of sulphuric acid may be adapted, e.g. per equivalent amine an additional equivalent of sulphuric acid may be used. Conveniently per g of a 7-[2-(aminothiazol-4-yl)-2-(tert.carboxymethoxyimino)-cetamido]-3-vinyl-3-cephem-4-carboxylic acid of formula IVA, such as of formula IV, e.g. 0.2 ml to 0.6 ml, such as 0.3 to 0.4 ml of e.g. 95% sulphuric acid may be used. The reaction temperature is not critical. The temperature may be below, about at, or above room temperature; such as from about 0° C. to about 80° C., e.g. from 0° C. to 80° C.; such as from 10° C. to 50° C., e.g. at room temperature. Higher temperatures may be used in case that $R_7$ and/or $R_{11}$ are not hydrogen and should be removed, to obtain a compound of formula II, e.g. simultanously cleaving $R_7$ and/or $R_{11}$ and $R_9$ in, e.g. a compound of formula IVA.

Any $R_7$ and/or $R_{11}$ which is other than hydrogen, e.g. as described above, may be removed to obtain a compound of formula IIA, wherein the amine group in the thiazolyl ring and/or the carboxylic group in position 4 of the ring system may be free, e.g. a compound of formula II, e.g. during sulphuric acid treatment, if appropriate in the presence of formic acid and/or acetic acid and/or water which may accelerate cleavage of e.g. protecting, groups; or by an appropriate e.g. conventional method.

A compound of formula IIA, wherein $R_7$, $R_{10}$ and $R_{11}$ are as defined above, e.g. a compound of formula II, in form of a crystalline sulphuric acid addition salt, e.g. in form of a hydrate, such as a monohydrate, may crystallise; addition of an anti-solvent to the reaction mixture, e.g. a nitrite, such as acetonitrile, may accelerate crystallisation. A sulphuric acid addition salt of cefixime of formula II may be obtained in form of a monohydrate, which may be de-hydrated, e.g. by drying. A sulphuric acid addition salt of cefixime of formula II with a water content of less than 2%, e.g. 1.3% and less, may be obtained, e.g. by drying in vacuo. A dried sulphuric acid addition salt of cefixime of formula II, exposed e.g. to normal atmospheric moisture, may absorb atmospheric moisture and a sulphuric acid addition salt of cefixime of formula II may be obtained having a water content of about e.g. 3.4 to 3.6%, which is close to the theoretical water content of a sulphuric acid addition salt of cefixime in form of a monohydrate, i.e. 3.16%.

A crystalline salt of cefixime of formula IIA, such as of formula II, with sulphuric acid in form of a monohydrate may surprisingly be obtained in an easily isolatable form in reaction step c., surprisingly in high purity, e.g. improving the purity of cefixime obtainable in a process according to the present invention. A crystalline salt of cefixime of formula IIA, e.g. of cefixime of formula II, with sulphuric acid, e.g. in form of a monohydrate is new and also forms part of the present invention.

In another aspect the present invention provides a sulphuric acid addition salt, e.g. in form of a solvate, such as a hydrate, e.g. monohydrate of a compound of formula IIA, wherein $R_7$, $R_{10}$ and $R_{11}$ are as defined above, e.g. of cefixime of formula II.

Step D. May Be Carried Out As Follows:

Conversion of a sulphuric acid addition salt of a compound of formula IIA, wherein $R_9$, $R_{10}$ and $R_{11}$ are as defined above, e.g. a sulphuric acid addition salt of a compound of formula II, into cefixime of formula II, e.g. in form of a solvate, such as a hydrate, e.g. trihydrate may e.g. be carried out as conventional in a conversion reaction of an acid addition salt of a compound into a that compound in free form, e.g. in the presence of a base, e.g. ammonia, a carbonate, e.g. sodium, potassium; a bicarbonate, e.g. sodium or potassium; a hydroxide; e.g. sodium or potassium, e.g. in solution, e.g. in water. A disodium, dipotassium or diammonium salt of a compound of formula IIA, e.g. cefixime of formula II, may be obtained. A compound of formula IIA, such as of formula II, may crystallise, e.g. in form of a soivate, e.g. a hydrate, such as a trihydrate, in the presence, e.g. by addition of an appropriate acid, e.g. as conventional, and, if desired in the presence of an organic solvent such as a ketone, e.g. acetone or an alcohol, e.g. ethanol.

A compound of formula IIA, e.g. cefixime of formula II, e.g. in form of a trihydrate may be also obtained directly from a reaction mixture containing e.g. a compound of formula IIA, e.g. cefixime of formula II in form of a sulphuric acid addition salt, e.g. in form of a hydrate, e.g. by neutralizing the sulphuric acid present in the reaction mixture, e.g. by addition of an appropriate base, e.g. as conventional.

From a compound of formula IIA, wherein $R_7$, $R_{10}$ and $R_{11}$ are as described above, any $R_7$, $R_{10}$ and $R_{11}$ which is other than hydrogen, may be removed to obtain a compound of formula IIA, wherein the amine group in the thiazolyl ring and/or the carboxylic group in position 4 of the ring system may be free, e.g. a compound of formula II, e.g. according to an, e.g., conventional method, either prior to conversion of a sulphuric acid addition salt of a compound of formula IIA, e.g. of formula II, into a compound of formula II in free form, e.g. in solvate form; or after such conversion.

2-(Aminothiazol-4-yl)-2-(tert.butoxycarbonylmethoxyimino)acetic acid S-mercapto-benzo-thiazolylester in form of an N,N-dimethylacetarnide solvate; and a crystalline salt of a 7-[2-(aminothiazol-4-yl)-2-(carboxymethoxyimino)acetamido]-3-vinyl-3-cephem-4-carboxylic acid of formula IA, wherein $R_7$, $R_9$, $R_{10}$ and R, are as defined above, with an amine of formula VI, wherein $R_1$, $R_2$ and $R_3$ are as defined above; and a sulphuric acid addition salt of a compound of formula IIA wherein $R_7$, $R_{10}$ and $R_{11}$ are as defined in claim 1 are useful compounds in a process for the production of cefixime of formula II because each of these compounds may show a high purification effect and each of these compounds may contribute to the purity of the end product cefixime in a process according to the present invention. According to a process of the present invention cefixime may be obtained in excellent purity and a process according to the present invention is useful for the purification of, e.g. impure, cefixime.

In another aspect the present invention provides the use of 2-(aminothiazol-4-yl)-2-(tert.butoxycarbonylmethoxyimino)acetic acid S-mercapto-benzo-thiazolylester in form of an N,N-dimethylacetamide solvate; and of a crystalline salt of a 7-[2-(aminothiazol-4-yl)-2-(carboxymethoxyimino)acetamido]-3-vinyl-3-cephem-4-carboxylic acid of formula IA, wherein $R_7$, $R_9$, $R_{10}$ and $R_{11}$ are as defined in claim 1, with an amine of formula VI, wherein $R_1$, $R_2$ and $R_3$ are as defined in claim 1; and of a sulphuric acid addition salt of a compound of formula IIA wherein $R_7$, $R_{10}$ and $R_{11}$, are as defined in claim 1 in a process for the production of cefixime of formula II.

In another aspect the present invention provides crystalline salts of 7-[2-(aminothiazol-4-yl)-2-(tert.butoxycarbonylmethoxyimino)atetamido]-3-vinyl-3-cephem-4-carboxylic acid of formula

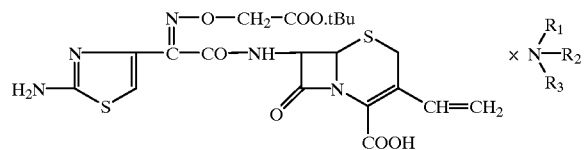

wherein $R_1$, $R_2$ and $R_3$ either each signify an ethyl group, or $R_1$ and $R_2$ are cyclohexyl and $R_3$ is hydrogen, or $R_1$ and $R_2$ are hydrogen and $R_3$ is the tert.octyl group.

In another aspect the present invention provides a crystalline salt of cefixime of formula

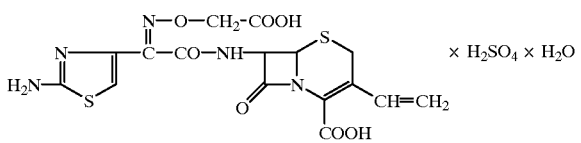

$\times H_2SO_4 \times H_2O$

In the following examples, which may illustrate the invention, but without limiting its scope, all temperatures are given in degrees Celsius.

EXAMPLE 1

2-(Aminothiazol-4-yl)-2-(tert.butoxycarbonylmethoxyimino)acetic Acid-S-mercaptobenzthiazolylester in Form of a Solvate with N,N-Dimethylacetamide 100 g of 2-(aminothiazol-4-yl)-2-(tert.butoxycarbonylmethoxyimino)acetic acid-S-mercaptobenzthiazolylester (Purity 96.9 in % of HPLC area) are dissolved in 200 ml of N,N-dimethylacetamide. 2-(Aminothiazol-4-yl)-2-(tert.butoxycarbonylmethoxyimino)acetic acid-S-mercaptobenzthiazolylester in form of a solvate with N,N-dimethylacetamide crystallises, the precipitate is filtrated off, washed with acetonitrile and dried.

Crystalline 2-(Aminothiazol-4-yl)-2-(tert.butoxycarbonylmethoxyimino)acetic acid-S-mercaptobenzthiazolylester in form of a solvate with N,N-dimethylacetamide is obtained.

Yield: 75.3 g; HPLC purity: 99.2 in % of area; M.p. (decomp.): 115–250°.

EXAMPLE 2

7-[2-(Aminothiazol-4-yl)-2-(tert.butoxycarbonylmethoxyimino)acetamido]-3-vinyl-3-cephem-4-carboxylic Acid in Form of a Salt with Tert.octylamine (2-Amino-2,4,4-trimethylpentane)

15 g of 7-amino-3-vinyl-3-cephem-4-carboxylic acid are suspended in 300 ml of ethyl acetate. 40 g of 2-(Aminothiazol-4-yl)-2-(tert.butoxycarbonylmethoxyimino)acetic acid-S-mercaptobenzthiazolylester in form of a solvate with N,N-dimethylacetamide in 30 ml of water are added to the reaction mixture. 8 g of triethylamine in 30 ml of ethyl acetate are added dropwise to the reaction mixture within ca. 1 hour. The reaction mixture is stirred for ca. 16 hours at room temperature and 300 ml of water are added. The phases formed are separated. To the aqueous phase 200 ml of ethyl acetate are added under stirring. The pH of the resulting mixture is adjusted to ca. 2.2 by addition of ca. 70–80 g of 75% phosphoric acid. The phases are separated and the aquepous phase is extracted with 200 ml of ethyl acetate.

To the combined ethyl acetate phases 12 g of tert.octylamine in 50 ml ethyl acetate are added within ca. 30 minutes under stirring. 7-[2-(Aminothiazol-4-yl)-2-(tert.butoxycarbonylmethoxyimino)acet-amido]-3-vinyl-3-cephem-4-carboxylic acid in form of a salt with tert.octylamine crystallises, the precipitate is filtrated off and dried.

Crystalline 7-[2-(Aminothiazol-4-yl)-2-(tert.butoxycarbonyimethoxyimino)acet-amido]-3-vinyl-3-cephem-4-carboxylic acid in form of a salt with tert.octylamine is obtained.

$^1$H NMR (MeOH-$d_4$): as in example 5 below.

EXAMPLE 3

7-[2-(Aminothiazol-4-yl)-2-(tert.butoxycarbonylmethoxyimino)acetamido]-3-vinyl-3-cephem-4-carboxylic Acid in Form of a Salt with Triethylamine 10 g of 7-[2-(aminothiazol-4-yl)-2-(tert.butoxycarbonylmethoxyimino)acetamido]-3-vinyi-3-cephem-4-carboxylic acid in 250 ml of ethyl acetate are treated with about 15 ml methanol under stirring. A solution obtained is treated dropwise with 2.1 g of triethylamine in 20 ml of ethyl acetate within ca. 20 minutes. 7-[2-(aminothiazol-4-yl)-2-(tert.butoxycarbonylmethoxyimino) acetamido]-3-vinyl-3-cephem-4-carboxylic acid in form of a salt with triethylamine crystallises, is filtrated off, washed with ethyl acetate and dried.

Crystalline 7-[2-(aminothiazol-4-yl)-2-(tert.butoxycarbonylmethoxyimino)acetamido]-3-vinyl-3-cephem-4-carboxylic acid in crystalline form of a salt with triethylamine is obtained. M.p.: Decomposition from 200°.

$^1$H NMR (MeOH-$d_4$): 7.08 (dd, J=11.2 und 17.6 Hz, 1H); 6.92 (s, 1H); 5.84 (d, 1H); 5.45 (d, 1H); 5.22 (d, 1H); 5.17 (d, 1H); 4.66 (s, 2H); 3.73 and 3.59 (AB, d, J=17.5 Hz, 1H); 3.19 (q, 2H); 1.48 (s, 9H); 1.30 (t, 3H).

EXAMPLE 4

7-[2-(Aminothiazol-4-yl)-2-(tert.butoxycarbonylmethoxyimino)acetamido]-3-vinyl-3-cephem-4-carboxylic Acid in Form of a Salt with Dicyclohexylamine 5.1 g of 7-[2-(aminothiazol-4-yl)-2-(tert.butoxycarbonylmethoxyimino)acetamido]-3-vinyl-3-cephem-4-carboxylic acid are dissolved in 50 ml of ethyl acetate, 5 ml of ethanol and 0.25 ml of water at 35°. 2 ml of dicyclohexylamine are added whilst stirring and the reaction mixture is seeded. 7-[2-(Aminothiazol-4-yl)-2-(tert.butoxycarbonylmethoxyimino)acetamido]-3-vinyl-3-cephem-4-carboxylic acid in form of a salt with dicyclohexylamine crystallises, the precipitate is filtrated off, washed with ethyl acetate and dried.

Crystalline 7-[2-(Aminothiazol-4-yl)-2-(tert.butoxycarbonylmethoxy-imino)acetamido]-3-vinyl-3-cephem-4-carboxylic acid in form of a salt with dicyclohexylamine is obtained.

$^1$H NMR (MeOH-$d_4$): 7.02 (dd, J=11.2 and 17.7 Hz, 1H); 6.92 (s, 1H); 5.79 (d, 1H); 5.31 (d, 1H); 5.12 (d, 1H); 5.10 (d, 1H); 4.65 (s, 2H); 3.65 and 3.54 (AB, d, J=17.3 Hz, 1H); 3.21–3.14 (m, 2H); 2.05 (m, 4H); 1.8 (m, 4H); 1.6 (m, 2H); 1.48 (s, 9H); 1.2–1.4 (m, 10H).

EXAMPLE 5

7-[2-(Aminothiazol-4-yl)-2-(tert.butoxycarbonylmethoxyimino)acetamido]-3-vinyl-3-cephem-4-carboxylic Acid in Form of a Salt with Tert.octylamine 5.1 g of 7-[2-(Aminothiazol-4-yl)-2-(tert.butoxycarbonylmethoxyiminonacetamido]-3-vinyl-3-cephem-4-carboxylic acid are dissolved in 50 ml of ethyl acetate, 10 ml of ethanol and 1 ml of water. The solution obtained is heated to 35° and seeded. 1.7 ml of tert.octylamine are added whilst stirring. 7-[2-(aminothiazol-4-yl)-2-(tert.butoxycarbonylmethoxyimino)acet-amido]-3-vinyl-3-cephem-4-carboxylic acid in form of a salt with tert.octylamine crystallises, is filtrated off, washed with ethyl acetate and dried.

Crystalline 7-[2-(aminothiazol-4-yl)-2-(tert.butoxycarbonylmethoxyimino)acetamido]-3-vinyl-3-cephem-4-carboxylic acid in form of a salt with tert.octylamine is obtained.

$^1$H NMR (MeOH-$d_4$): 7.02 (dd, J=11.2 and 17.7 Hz, 1H); 6.92 (s, 1H); 5.79 (d, 1H); 5.32 (d, 1H); 5.13 (d, 1H); 5.11 (d, 1H); 4.65 (s, 2H); 3.66 and 3.55 (AB, d, J=17.3 Hz, 1H); 1.66 (s, 2H); 1.49 (s, 9H); 1.43 (s, 6H); 1.06 (s, 9H).

EXAMPLE 6

7-[2-(Aminothiazol-4-yl)-2-(tert.butoxycarbonylmethoxyimino)acetamido]-3-vinyl-3- cephema4-carboxylic Acid in Form of a Salt with Tert.octylamine (Directly From Acylation Reaction Mixture)

20 g of 7-Amino-3-vinyl-3-cephem-4-carboxylic acid are suspended at room temperature in 200 ml of dichloromethane. 45 g of 2-(Aminothiazol-4-yl)-2-(tert.butoxycarbonylmethoxy-imino)acetic acid-S-mercaptobenzothiazolyl-ester, 4 ml of water and 10 9 of triethyl-amine are added to the reaction mixture and the mixture is heated to ca. 30° to 35° under reflux. An almost clear solution is obtained within ca. 3.5 hours. 5 ml of methanol are added and the mixture is filtered. The filtrate is heated to ca. 35° and a solution of 22 g of tert.octylamine in 100 ml of dichloromethane is added. Crystallisation starts e.g. after seeding. Ca. 100 ml of solvent are distilled off and ca. 200 ml of dichloromethane are simultaneously added. The suspension obtained is cooled to −10°. Crystalline 7-[2-(aminothiazol-4-yl)-2-(tert.butoxycarbonylmethoxyimino)acetamido]-3-vinyl-3-cephem-4-carboxylic acid in form of a salt with tert.octylamine precipitates, is filtrated off, washed with cooled (−20°) dichloromethane, and dried.

Crystalline 7-[2-(aminothiazol-4-yl)-2-(tert.butoxycarbonylmethoxyimino)acetamido]-3-vinyl-3-cephem-4-carboxylic acid in form of a salt with tert.octylamine is obtained.

M.p.: 190° (decomp.); Content of by-products: 0.23%; Content of free cefixime: 0.03%; $^1$H NMR (MeOH-$d_4$): As described in Example 5.

EXAMPLE 7

7-[2-(Aminothiazol-4-yl)-2-(tert.butoxycarbonylmethoxyimino)acetamido]-3-vinyl-3-cephem-4-carboxylic Acid in Form of a Salt with Triethylamine (Directly From Acylation Reaction Mixture)

10 g of 7-Amino-3-vinyl-3-cephem-4-carboxylic acid are suspended in 100 ml of dichloromethane and the suspension obtained is cooled to 0°. 10 ml of water are added and 10 g of triethylamine are added dropwise to the reaction mixture. The temperature of the reaction mixture is adjusted to ca. ca. 20° and 22 g of 2-(aminothiazol-4-yl)-2-(tert.butoxycarbonylmethoxyimino)acetic acid-S-mercaptobenzothiazolyl-ester are added. The reaction mixture is stirred further for 3 hours at room temperature. 7-[2-(Aminothiazol-4-yl)-2-(tert.butoxycarbonylmethoxyimino)acetamido]-3-vinyl-3-cephem-4-carboxylic acid in form of a salt with triethylamine precipitates, is filtrated off, stirred in 100 ml of dichloromethane, filtrated off and dried.

Crystalline 7-[2-(aminothiazol-4-yl)-2-(tert.butoxycarbonylmethoxyimino)acetamido]-3-vinyl-3-cephem-4-carboxylic acid in form of a salt with triethylamine is obtained.

$^1$H NMR (MeOH-$d_4$): As described in Example 3.

REFERENCE EXAMPLE

7-[2-(Aminothiazol-4-yl)-2-(tert.butoxycarbonylmethoxyimido]-3-vinyl-3-cephem-4-carboxylic Acid 0.982 kg of triethylamine and 2.56 kg of 2-(aminothiazol-4-yl)-2-(tert.butoxycarbonylmethoxyimino)acetic acid-S-mercaptobenzothiazolyl-ester are added to a mixture of 1.044 kg of 7-amino-3-vinyl-cephem-4-carboxylic acid, 25.4 l of ethyl acetate, 0.94 l of water and 2.4 l of methanol, cooled to 10°, under stirring. The reaction mixture obtained is cooled to 2° and stirred for 20 hours. A clear solution is obtained, which is mixed with 23.4 l of water and stirred for 20 minutes. The reaction mixture is heated to 20°. 3.5 N Hydrochloric acid is added and a pH between ca. 2.0 and 2.3 is adjusted. The phases formed are separated and the aqueous phase is extracted with ethyl acetate. 0.234 kg of activated carbon are added to the combined ethyl acetate phases under stirring and activated carbon is filtrated off. 23.4 l of water are added to the filtrate and the pH is adjusted to 8.0 by addition of ca. 0.93 l of 5 N sodium hydroxide solution. The phases are separated and the organic phase is extracted with water. Ethyl acetate traces in the mixture are removed by evaporation. The aqueous phase is mixed with 0.053 kg of activated carbon under stirring and activated carbon is filtrated off. 6 N Hydrochloric acid is added to the reaction mixture and a pH of about 2.3 is adjusted. The suspension is cooled to 5° and stirred for 30 minutes at that temperature. 7-[2-(aminothiazol-4-yl)-2-(tert.butoxycarbonylmethoxyimino)acetamido]-3-vinyl-3-cephem-4-carboxylic acid precipitates, is isolated by centrifugation, washed with water and dried.

7-[2-(aminothiazol-4-yl)-2-(tert.butoxycarbonylmethoxyimino)acetamido]-3-vinyl-3-cephem-4-carboxylic acid in solid form is obtained.

HPLC content: 85.9%; $H_2O$: 4.3%; Free cefixime: 1.6%; Purity in % of HPLC area: 92.84%.

EXAMPLE 8

Sulphuric Acid Addition Salt of 7-[2-(2-Aminothiazol-4-yl)-2-carboxymethoxyimino)acetamido]-3-vinyl-3-cephem-4-carboxylic Acid in Form of a Monohydrate To a mixture of 40 g of 7-[2-(aminothiazol-4-yl)-2-(tert.butoxycarbonylmethoxyimino)-acetamido]-3-vinyl-3-cephem-4-carboxylic acid, 40 ml of formic acid and 400 ml of acetonitrile, 12 ml of 95% H2SO4 are added at room temperature. A sulphuric acid addition salt of 7-[2-(2-aminothiazol-4-yl)-2-carboxymethoxyimino)acetamido]-3-vinyl-3-cephem-4-carboxylic acid in form of a monohydrate crystallizes, is filtrated off, washed with acetonitrile and dried.

A crystalline sulphuric acid addition salt of 7-[2-(2-aminothiazol-4-yl)-2-carboxymethoxy-imino)acetamido]-3-vinyl-3-cephem-4-carboxylic acid in form of a monohydrate is obtained.

Cefixime content: 76.3% (HPLC); $H_2SO_4$ content: 19.0% (ion chromatography); Acetonitrile content: 0.84% (GC); Water content: 1.3% (KF).

A part of 7-[2-(2-aminothiazol-4-yl)-2-carboxymethoxyimino)-acetamido]-3-vinyl-3-cephem-4-carboxylic acid in form of a monohydrate, obtained after drying is equilibrated in air over night. Water content: 3.4% (KF).

EXAMPLE 9

Sulphuric Acid Addition Salt of 7-[2-(2-Aminothiazol-4-yl)-2-carboxymethoxy-imino)acetamido]-3-vinyl-3-cephem-4-carboxylic Acid in Form of a Monohydrate To a solution of 20 g of 7-[2-(aminothiazol-4-yl)-2-(tert.butoxycarbonylmethoxyimino)acet-amido]-3-vinyl-3-cephem-4-carboxylic acid in form of a salt with tert.octylamine, 20 ml of formic acid and 200 ml of acetonitrile. 8 ml of 95% $H_2SO_4$ are added dropwise within 5 minutes and the mixture is seeded and stirred at room temperature and in an ice bath. A sulphuric acid addition salt of 7-[2-(2-aminothiazol-4-yl)-2-carboxymethoxyimino)-acetamido]-3-vinyl-3-cephem-4-carboxylic acid in form of a monohydrate crystallizes, is filtrated off, washed with acetonitrile and dried.

A crystalline sulphuric acid addition salt of 7-[2-(2-aminothiazol-4-yl)-2-carboxymethoxy-imino)-acetamido]-3-vinyl-3-cephem-4-carboxylic acid in form of a monohydrate is obtained.

Purity (HPLC): 99% (in % of HPLC area); Cefixime content: 75.7% (HPLC); $H_2SO_4$ content: 18.6% (ion chromatography); Acetonitrile content: 1.8% (GC); Water content: 1.9% (KF).

EXAMPLE 10

Cefixime Production From a Sulphuric Acid Addition Salt in Form of a Monohydrate 14.87 g of a sulphuric acid addition salt of 7-[2-(2-aminothiazol-4-yl)-2-carboxymethoxy-imino)acetamido]-3-vinyl-3-cephem-4-carboxylic acid in form of a monohydrate are suspended in 148 ml of water and diluted ammonia is added to adjust a pH of 6.0. 2.97 g of activated carbon are added, the reaction mixture is stirred at room temperature and activated carbon is filtered off. The filtrate is diluted with water to give a total volume of about 600 ml, mixed with 300 ml of ethanol and heated to 28°. The pH is adjusted to ca. 3.5 by addition of 6 N HCl. Seeding crystals are added. Cefixime in form of a trihydrate crystallizes. The resultant suspension is stirred for one hour at 28°, the pH is adjusted to ca. 2.5 and the suspension is stirred at room temperature and in an ice bath. Crystalline cefixime in form of a trihydrate is filtrated off, washed with water and dried.

Crystalline cefixime in form of a trihydrate is obtained.
Purity (HPLC):99.4 in % of HPLC area.

What is claimed is:

1. A process for the production of cefixime of formula

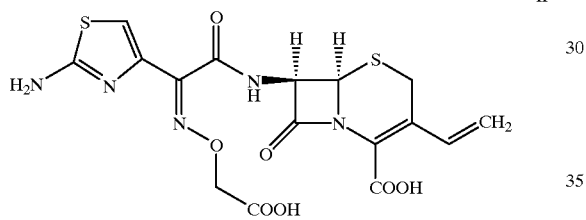

comprising a. reacting a 7-amino-3-vinyl-3-cephem-4-carboxylic acid of formula

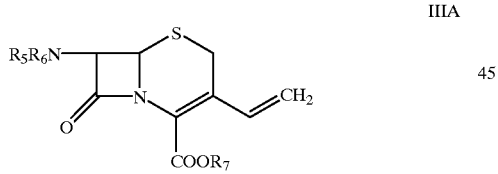

wherein $R_5$ denotes hydrogen or a leaving group, $R_6$ denotes hydrogen and $R_7$ denotes hydrogen, alkyl, cycloalkyl, alkylaryl, aryl, arylalkyl or a silyl protecting group; with a 2-(aminothiazol-4-yl)-2-carboxymethoxyimino)acetic acid ester of formula

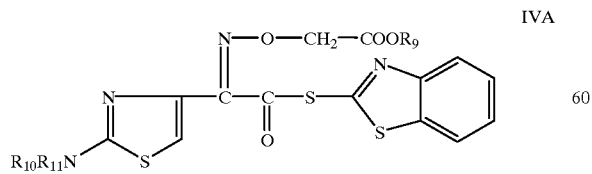

in free form or in form of a salt or a solvate,
wherein $R_9$ denotes alkyl, cycloalkyl, alkylaryl, aryl or arylalkyl, $R_{10}$ denotes hydrogen and $R_{11}$ denotes hydrogen, a silyl protecting group or $(C_{1-24})$ carboxylic acid acyl group, to give a 7-[2-(aminothiazol-4-yl)-2-(carboxy-methoxyimino) acetamido]-3-vinyl-3-cephem-4-carboxylic acid of formula

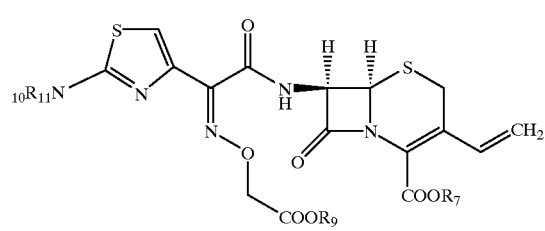

wherein $R_7$, $R_9$, $R_{10}$ and $R_{11}$ are as defined above, b. reacting a 7-[2-(aminothiazol-4-yl)-2-(carboxymethoxyimino)-acetamido]-3-vinyl-3-cephem-4-carboxylic acid of formula IA, wherein $R_7$ is H and $R_9$, $R_{10}$ and $R_{11}$ are as defined above, with an amine of formula

wherein $R_1$, $R_2$ and $R_3$ independently of each other denote hydrogen, alkyl, cycloalkyl, alkylaryl, aryl or aralkyl, to give a crystalline salt of a compound of formula IA, wherein $R_7$ is H and $R_9$, $R_{10}$ and $R_{11}$ are as defined above with an amine of formula VI, wherein $R_1$, $R_2$ and $R_3$ are as defined above, c. reacting said crystalline salt of a compound of formula IA, wherein $R_7$ is H and $R_9$, $R_{10}$ and $R_{11}$ are as defined above with an amine of formula VI, wherein $R_1$, $R_2$ and $R_3$ are as defined above, with sulphuric acid to obtain a compound of formula

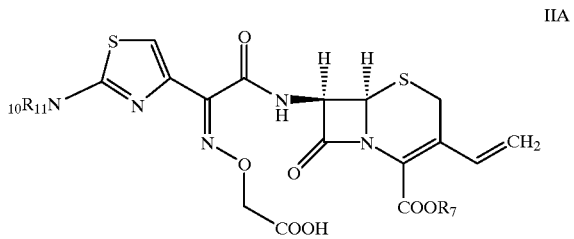

wherein $R_7$ is H and $R_{10}$ and $R_{11}$ are as defined above, in form of a crystalline sulphuric acid addition salt, and, d. converting a sulphuric acid addition salt of 7-[2-(aminothiazol-4-yl)-2-(carboxy-methoxyimino) acetamido]-3-vinyl-3-cephem-4-carboxylic acid of formula IIA, wherein $R_7$ is H and $R_{10}$ and $R_{11}$ are as defined above, into cefixime of formula II, and optionally e. removing $R_{11}$ if other than hydrogen

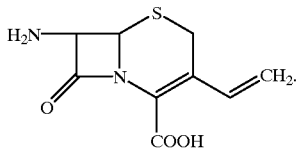

III

2. A process according to claim 1, wherein a compound of formula IIIA is 7-amino-3-vinyl-3-cephem-4-carboxylic acid of formula

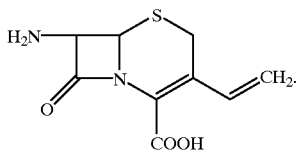

III

3. A process according to claim 1, wherein a compound of formula IVA is 2-(aminothiazol-4-yl)-2-(tert.butoxycarbonyl-methoxyimino)acetic acid S-mercaptobenzothiazolylester of formula

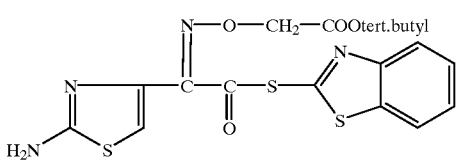

IV in form of an N,N-dimethylacetamide solvate.

4. A process according to any one of claim 1, wherein cefixime of formula II is in form of a trihydrate.

5. 2-(Aminothiazol-4-yl)-2-(tert.butoxycarbonylmethoxyimino)acetic acid S-mercaptobenzo-thiazolylester of formula IV in form of an N,N-dimethylacetamide solvate.

6. A crystalline salt of a 7-[2-(aminothiazol-4-yl)-2-(carboxymethoxyimino)acetamido]-3-vinyl-3-cephem-4-carboxylic acid of formula IA, wherein $R_7$ is H and $R_9$, $R_{10}$ and $R_{11}$ are as defined in claim 1, with an amine of formula VI, wherein $R_1$, $R_2$ and $R_3$ are as defined in claim 1.

7. A salt according to claim 6, wherein a 7-[2-(aminothiazol-4-yl)-2-(carboxymethoxyimino)acetamido]-3-vinyl-3-cephem-4-carboxylic acid of formula IA is 7-[2-(aminothiazol-4-yl)-2-(butoxycarbonylmethoxyimino) acetamido]-3-vinyl-3-cephem-4-carboxylic acid of formula

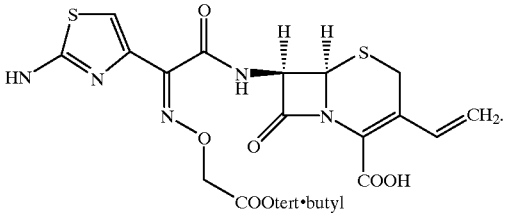

I

8. A salt according to claim 6 which is a salt of 7-[2-(aminothiazol-4-yl)-2-(tert.butoxycarbonylmethoxyimino) acetamido]-3-vinyl-3-cephem-4-carboxylic acid with triethylamine, dicyclohexylamine or tert.octylamine.

9. A sulphuric acid addition salt of a compound of formula IIA wherein $R_7$ is H and $R_{10}$ and $R_{11}$ are as defined in claim 1.

10. A salt according to claim 9, wherein a compound of formula IIA is cefixime of formula II.

11. A crystalline salt of cefixime of formula

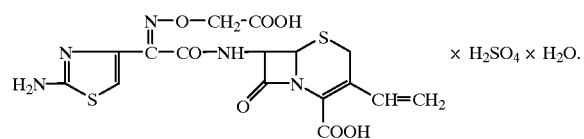

I

12. Crystalline salts of 7-[2-(aminothiazol-4-yl)-2-(tert.butoxy-carbonylmethoxyimino)acetamido]-3-vinyl-3-cephem-4-carboxylic acid of formula wherein $R_1$, $R_2$ and $R_3$ either each signify an ethyl group, or $R_1$ and $R_2$ are cyclohexyl and $R_3$ is hydrogen, or $R_1$ and $R_2$ are hydrogen and $R_3$ is the tert.octyl group.

* * * * *

UNITED STATES PATENT AND TRADEMARK OFFICE
CERTIFICATE OF CORRECTION

PATENT NO. : 6,313,289 B1
DATED : November 6, 2001
INVENTOR(S) : Ludescher et al.

Page 1 of 1

It is certified that error appears in the above-identified patent and that said Letters Patent is hereby corrected as shown below:

<u>Column 17,</u>
Line 38, should read: -- A process according to claim 1, wherein cefixime of formula II is in form of a trihydrate. --

Signed and Sealed this

Twenty-first Day of May, 2002

Attest:

JAMES E. ROGAN
*Director of the United States Patent and Trademark Office*

*Attesting Officer*